US011016075B2

(12) United States Patent
Alvarez et al.

(10) Patent No.: US 11,016,075 B2
(45) Date of Patent: May 25, 2021

(54) METHODS AND SYSTEMS FOR CHARACTERIZATION OF GEOCHEMICAL PROPERTIES OF HYDROCARBONS USING MICROWAVES

(71) Applicant: Saudi Arabian Oil Company, Dhahran (SA)

(72) Inventors: Jose Oliverio Alvarez, Houston, TX (US); David Jacobi, Houston, TX (US)

(73) Assignee: SAUDI ARABIAN OIL COMPANY

( * ) Notice: Subject to any disclaimer, the term of this patent is extended or adjusted under 35 U.S.C. 154(b) by 324 days.

(21) Appl. No.: 16/039,037

(22) Filed: Jul. 18, 2018

(65) Prior Publication Data

US 2019/0025275 A1  Jan. 24, 2019

Related U.S. Application Data

(60) Provisional application No. 62/535,053, filed on Jul. 20, 2017.

(51) Int. Cl.
*G01N 33/28* (2006.01)
*G01N 22/00* (2006.01)
*E21B 49/08* (2006.01)

(52) U.S. Cl.
CPC ............ *G01N 33/28* (2013.01); *G01N 22/00* (2013.01); *G01N 33/2823* (2013.01); *E21B 49/08* (2013.01)

(58) Field of Classification Search
CPC .... G01N 33/28; G01N 33/2823; G01N 22/00; E21B 49/08
USPC ............................... 436/29–30, 139–142, 60
See application file for complete search history.

(56) References Cited

U.S. PATENT DOCUMENTS

| | | | | |
|---|---|---|---|---|
| 3,778,706 A | * | 12/1973 | Thompson | G01N 27/221 324/668 |
| 4,764,718 A | * | 8/1988 | Revus | G01N 22/00 324/637 |
| 4,817,711 A | * | 4/1989 | Jeambey | E21B 43/2401 166/248 |
| 5,083,089 A | * | 1/1992 | Yuki | G01N 33/2823 324/632 |
| 5,103,181 A | * | 4/1992 | Gaisford | G01N 33/2823 324/637 |
| 5,124,653 A | * | 6/1992 | Andresen | G01N 22/00 324/633 |

(Continued)

OTHER PUBLICATIONS

Xiao, J., Geochemistry 1985, 4, 67-76.*
Sen, A. D. et al, Journal of Physics D: Applied Physics 1992, 25, 516-521.*
Goual, L. et al, AIChE Journal 2002, 48, 2646-2663.*
Francisca, F. M. et al, Journal of Environmental Engineering 2003, 129, 347-357.*

(Continued)

*Primary Examiner* — Arlen Soderquist
(74) *Attorney, Agent, or Firm* — Bracewell LLP; Constance Gall Rhebergen

(57) ABSTRACT

Provided here are methods, apparatuses, and systems directed to the determination of geochemical properties of liquid hydrocarbons based on the dielectric properties of components of the liquid hydrocarbons using microwaves. Also disclosed is a method for characterizing a geochemical property of a liquid hydrocarbon by measuring the dielectric responses from a portion of the liquid hydrocarbon at different predetermined temperatures in two or more microwave resonant cavities to electromagnetic waves at select microwave frequencies, and determining a geochemical property of the liquid hydrocarbon in response to measurements of the dielectric responses.

20 Claims, 14 Drawing Sheets

(56) References Cited

U.S. PATENT DOCUMENTS

| | | | |
|---|---|---|---|
| 6,449,580 B1* | 9/2002 | Bardetsky | G01N 33/2888 702/127 |
| 7,748,265 B2 | 7/2010 | Reid et al. | |
| 9,335,273 B2 | 5/2016 | Botto et al. | |
| 2003/0122555 A1* | 7/2003 | Baron | G01N 27/221 324/668 |
| 2003/0155926 A1* | 8/2003 | May | G01N 22/00 324/460 |
| 2004/0075448 A1* | 4/2004 | Lvovich | G01N 33/2888 324/707 |
| 2005/0264302 A1* | 12/2005 | Mohajer | G01R 27/22 324/639 |
| 2007/0224692 A1* | 9/2007 | Agar | G01N 27/22 436/150 |
| 2009/0261987 A1* | 10/2009 | Sun | G01N 27/414 340/870.07 |
| 2011/0057653 A1* | 3/2011 | Barmatz | G01R 33/1223 324/316 |
| 2013/0111980 A1* | 5/2013 | Soergel | G01N 33/2852 73/61.61 |
| 2013/0283892 A1 | 10/2013 | Parker | |
| 2014/0116117 A1* | 5/2014 | Joksch | G01N 27/22 73/61.44 |
| 2014/0182737 A1* | 7/2014 | Jones | G01F 1/32 138/177 |
| 2015/0097561 A1 | 4/2015 | Desmulliez et al. | |
| 2015/0168312 A1* | 6/2015 | Wendt | G01N 33/2835 73/61.44 |
| 2015/0226683 A1* | 8/2015 | Feldman | G01N 27/023 324/640 |
| 2015/0346131 A1* | 12/2015 | Mohseni | G01N 27/026 324/663 |
| 2015/0355110 A1 | 12/2015 | Sappok et al. | |
| 2016/0161029 A1 | 6/2016 | Jones et al. | |
| 2016/0161425 A1 | 6/2016 | Berezin et al. | |
| 2017/0138922 A1* | 5/2017 | Potyrailo | G01M 13/021 |
| 2019/0029555 A1* | 1/2019 | Suster | G01N 27/08 |

OTHER PUBLICATIONS

Feng, X.-L. et al, Journal of Logistical Engineering University 2005, 46-49.*
Guan, L. et al, Fuel 2009, 88, 1453-1459.*
Ateeq, M. et al, Measurement Science and Technology 2012, 23, paper 0855503, 13 pages.*
Muley, P. D. etal, Bioresource Technology 2013, 127, 165-174.*
De Souza, J. E. et al, Fuel 2013, 105, 705-710.*
Ulrych, J. et al, 2014 IEEE 18th International Conference on Dielectric Liquids 2014, 1-4.*
De Graaf, G. et al, 2015 IEEE International Instrumentation and Measurement Technology Conference (I2MTC) Proceedings 2015, 154-158.*
Abdolrazzaghi, M. et al, IEEE Sensors 2016, 1-3.*
Alvarez, J. O. et al, 2017 IEEE International Geoscience and Remote Sensing Symposium 2017, 365-368.*
Folgero, K. et al, Measurement Science and Technology 1995, 6, 995-1008.*
Feng, X.-L. et al, Journal of Logistical Engineering University 2005, 46-49 with English translation.*
Rowe, D. J. et al, Sensors and Actuators B 2012, 169, 213-221.*
Helmy, A. A. et al, IEEE Transactions on Microwave Theory and Techniques 2012, 60, 4157-4170.*
Bakhshiani, M. et al, IEEE Journal of Solid-State Circuits 2014, 49, 1669-1681.*
Bajestan, M. M. et al, IEEE Transactions on Microwave Theory and Techniques 2014, 62, 3522-3537.*
Folgero, K. "Broad-Band Dielectric Spectroscopy of Low-Permittivity Fluids Using One Measurement Cell," IEEE Trans. Instrum. Meas., vol. 47, No. 4, pp. Aug. 1998, pp. 881-885.
May, E, et al.; "Density, Dielectric constant and PVT measurements of a gas condensate fluid," Journal of Petroleum Science Engineering, vol. 41, 2004; pp. 297-308.
The International Search Report and Written Opinion for related PCT application PCT/US2018/042787 dated Nov. 14, 2018.

* cited by examiner

METHODS AND SYSTEMS FOR CHARACTERIZATION OF GEOCHEMICAL PROPERTIES OF HYDROCARBONS USING MICROWAVES

CROSS-REFERENCE TO RELATED APPLICATION

This application claims the priority to, and benefit of, U.S. Provisional Application No. 62/535,053, filed on Jul. 20, 2017, and the contents of this application are hereby incorporated by reference in their entirety.

FIELD

The disclosure relates to methods, apparatuses, and systems generally directed to the geochemical analysis of fluids using microwave measurements and the dielectric properties of components of the fluids.

BACKGROUND

Dielectric spectroscopy of reservoir rock samples requires the knowledge of the dielectric properties of each component of the matrix. These components include fluids in the pores. Naturally, emphasis is given to the presence of water, the fluid with the greatest permittivity. Its greater dielectric constant, as compared to other fluids from the reservoir rock pores, allows for easier determination of the presence of water in the hydrocarbons, which is a major factor in determining economic life of a well. Applications of dielectric properties of reservoir fluids have until recently focused mainly in water cut metering or on-line water determination. The composition of hydrocarbons produced or recovered from conventional and unconventional reservoirs changes according to source, maturity, biodegradation, evaporative fractionation, and treatments, such as thermal chemical sulfate reduction. All of these processes can have a significant effect on the molecular composition of the oil produced and its physical properties, like viscosity and density. Moreover, changes in these fluid properties occurring during production could signal the fouling of the wellbore with precipitation of wax or formation damage or both. To obtain a complete geochemical analysis of a hydrocarbon sample, several tests are needed, such as saturate-aromatic-resin-asphaltene analysis (SARA), gas chromatography (GC), and the gas chromatography mass spectroscopy (GCMS). The causes of these changes in the produced fluids are often discovered after they have already occurred, typically using laboratory analysis. These methods are time consuming, and often do not aid in real time monitoring of changes in composition.

SUMMARY

Several disadvantages of existing technologies were recognized and various embodiments of this disclosure were developed to address these shortcomings in the art. The interplay of the microwave measurements and the dielectric properties of components of hydrocarbons have been exploited to analyze the properties of produced hydrocarbons and to monitor for changes that can occur during production.

Certain embodiments disclosed and described here include methods for evaluating or characterizing a geochemical property of a liquid hydrocarbon. One such method includes exposing a portion of the liquid hydrocarbon at a predetermined temperature in two or more microwave resonant cavities to electromagnetic waves at two or more microwave frequencies to elicit two or more dielectric responses from the portion of the liquid hydrocarbon. Two or more dielectric responses are then measured from the portion of the liquid hydrocarbon in response to the electromagnetic waves at the two or more microwave frequencies. A geochemical property of the liquid hydrocarbon is determined in response to measurements of the two or more dielectric responses. In certain embodiments, the liquid hydrocarbon sample is maintained at the predetermined temperature during the step of measuring the two or more dielectric responses. The liquid hydrocarbon that is subject to analysis can be an oil separated from a production fluid containing brine and oil. The two or more microwave resonant cavities can be configured to hold a vial made of quartz or sapphire. The two or more microwave resonant cavities can be of different sizes and provide for different microwave frequencies ranges. These microwave frequencies can range from 100 megahertz (MHz) to 20 gigahertz (GHz). In certain embodiments, the microwave frequencies range from 170 MHz to 8.6 GHz. The geochemical property of the hydrocarbon, which is evaluated using these methods, can be one or more of saturates content, aromatics content, resins content, or asphaltenes content of the liquid hydrocarbon. In some embodiments, the geochemical property that is evaluated can be heptane content, toluene content, or xylenes content, or toluene to heptane ratio, or xylenes to heptane ratio of the liquid hydrocarbon.

Certain embodiments disclosed and described here include methods for evaluating or characterizing a geochemical property of a liquid hydrocarbon at two or more predetermined temperatures. In one such method for characterizing a geochemical property of a liquid hydrocarbon, a portion of the liquid hydrocarbon is exposed at a first predetermined temperature in a low frequency microwave resonant cavity to electromagnetic waves at a first set of two or more microwave frequencies to elicit a first set of two or more dielectric responses from the portion of the liquid hydrocarbon. In an embodiment, the low frequency microwave resonant cavity is responsive to frequencies ranging from 100 MHz to 2.3 GHz. In an embodiment, the low frequency microwave resonant cavity is responsive to frequencies ranging from 170 MHz to 2.3 GHz. The first set of two or more dielectric responses from the portion of the liquid hydrocarbon in response to the electromagnetic waves at the first set of two or more microwave frequencies are measured. The portion of the liquid hydrocarbon at the first predetermined temperature in a high frequency microwave resonant cavity is then exposed to electromagnetic waves at a second set of two or more microwave frequencies to elicit a second set of two or more dielectric responses from the portion of the liquid hydrocarbon. In an embodiment, the high frequency microwave resonant cavity is responsive to frequencies ranging from 1.3 GHz to 20 GHz. In an embodiment, the high frequency microwave resonant cavity is responsive to frequencies ranging from 1.3 GHz to 8.6 GHz. The second set of two or more dielectric responses from the portion of the liquid hydrocarbon in response to the electromagnetic waves at the second set of two or more microwave frequencies are measured. The method further includes exposing the portion of the liquid hydrocarbon at a second predetermined temperature in the low frequency microwave resonant cavity to electromagnetic waves at a third set of two or more microwave frequencies to elicit a third set of two or more dielectric responses from the portion of the liquid hydrocarbon. The third set of two or more dielectric responses from the portion of the liquid hydrocarbon in response to the electromagnetic waves at the third set of two or more microwave frequencies are measured. The portion of the liquid hydrocarbon is then exposed at a third predetermined temperature in the high frequency microwave resonant cavity to electromagnetic waves at a fourth set of two or more microwave frequencies to elicit a fourth set of two or more dielectric responses from the portion of the liquid hydrocarbon. The fourth set of two or more dielectric responses from the portion of the liquid hydrocarbon in response to the electromagnetic waves at the fourth set of two or more microwave frequencies are measured. A geochemical property of the liquid hydrocarbon is determined in response to measurements of the first set, the second set, the third set, and the fourth set of the two or more dielectric responses.

The liquid hydrocarbon that is subject to analysis can be an oil separated from a production fluid containing brine and oil. The cavities can be configured to hold a sample vial made of quartz or sapphire. The low frequency microwave resonant cavity can provide for five microwave frequencies. The high frequency microwave resonant cavity can provide for four microwave frequencies. The two or more microwave frequencies can range from 100 MHz to 20 GHz. The first set of the two or more microwave frequencies and the third set of the two or more microwave frequencies can range from 170 MHz to 2.3 GHz. The second set of the two or more microwave frequencies and the fourth set of the two or more microwave frequencies can range from from 1.3 GHz to 8.6 GHz.

The geochemical property of the hydrocarbon, which is evaluated using these methods, is one or more of saturates content, aromatics content, resins content, or asphaltenes content present in the liquid hydrocarbon. In certain embodiments, the geochemical property that is evaluated is one or more of toluene content, or xylenes content, heptane content, ratio of toluene to heptane, or ratio of xylenes to heptane present in the liquid hydrocarbon. The geochemical property can be a ratio of metal content associated with porphyrins to sulfur content present in the liquid hydrocarbon. Results from evaluation of the hydrocarbons using these methods can be used to characterize the liquid hydrocarbon and better understand the composition and changes that occur during evaluation of the formation, discovery drilling, developmental drilling, production, enhanced recovery, abandonment, or reclamation.

Numerous other aspects, features and benefits of the present disclosure may be apparent from the following detailed description taken together with the drawings. The systems can include fewer components, or more components, or different components depending on desired analytical results.

BRIEF DESCRIPTION OF THE DRAWINGS

Embodiments will be readily understood by the following detailed description in conjunction with the accompanying drawings. The drawings may not be to scale. Embodiments are illustrated by way of example and not by way of limitation in accompanying drawings.

FIGS. 2A, 2C, and 2E are the mass spectrums obtained for the three samples following GCMS analysis, while

DETAILED DESCRIPTION

Figure 1:
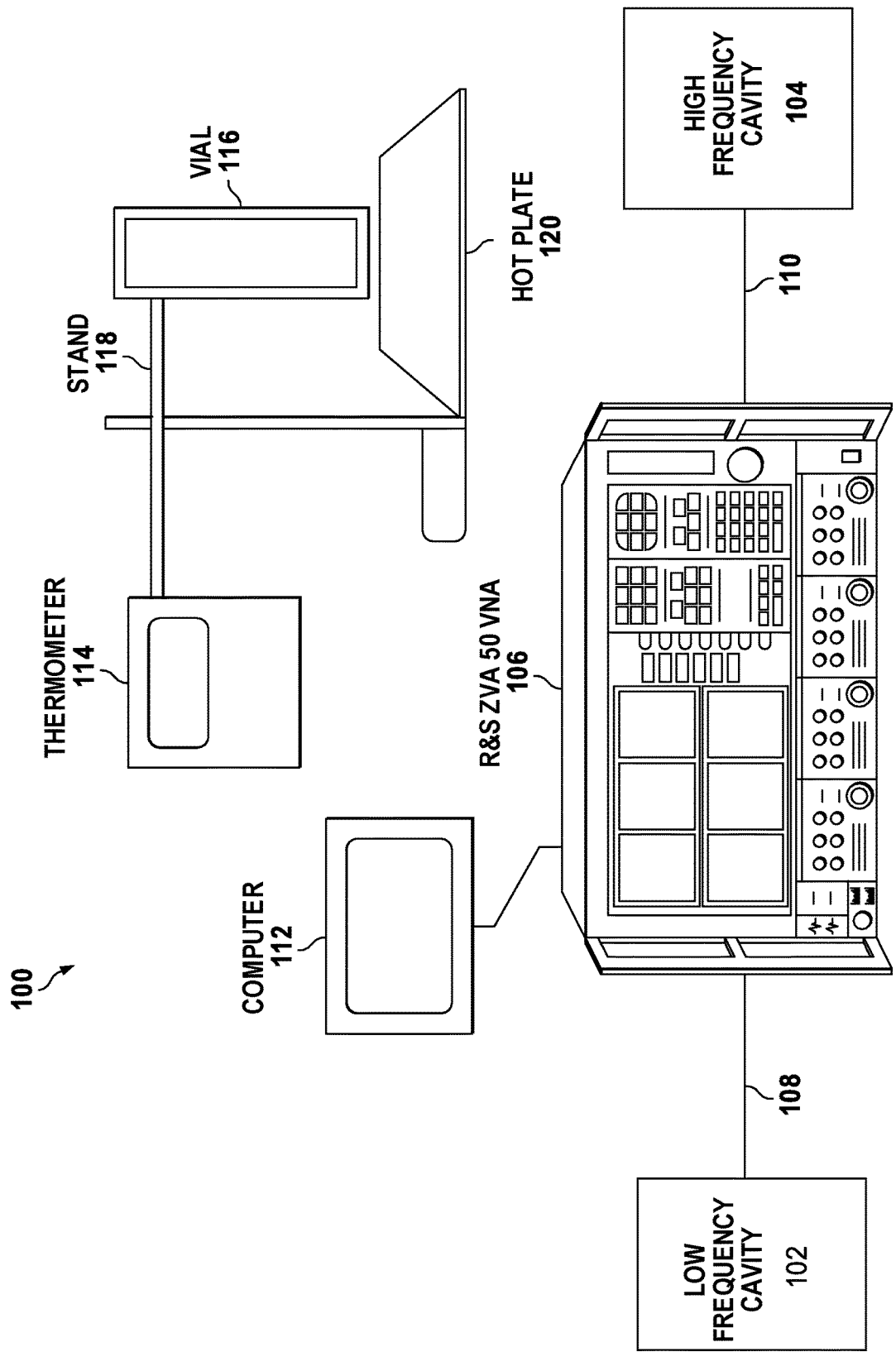
FIG. 1 is a diagrammatic representation of a system with two resonant cavities, according to an embodiment.

The present disclosure describes various embodiments related to methods, apparatuses, and systems generally directed to the geochemical analysis of fluids, especially hydrocarbons, using microwave measurements and the dielectric properties of components of the fluid. Certain aspects of the disclosure include methods and systems for prediction of the properties of liquid hydrocarbons based on utilization of multipoint resonant cavities to obtain accurate values of complex permittivity for the liquid hydrocarbons. Certain aspects of the disclosure include methods and systems that integrate the real and imaginary aspects of relative permittivity analysis to determine the differences in geochemistry and physical properties of the hydrocarbon samples and any changes in the hydrocarbon components of the samples during production.

Using the dielectric/permittivity spectra from liquid hydrocarbons to characterize their composition requires knowledge of their geochemistry and the geological processes that formed them. Microwave characterization of liquid hydrocarbons presents a faster way to characterize and screen the geochemical properties of a hydrocarbon fluid, such as API gravity (American Petroleum Institute gravity), maturity, and quality. However, as the fluids have low conductivity, resonant methods were utilized to obtain accurate readings for both the real and imaginary part of the permittivity. Disclosed here are the uses of multipoint resonant cavities in the analysis of crude oil samples at different temperatures to characterize the geochemical composition. Embodiments include methods of characterization of the hydrocarbons using complex permittivity measurements at predetermined temperatures using at least two or more multipoint resonant cavities. These methods were able to characterize both crude oil and gas condensate samples. In certain embodiments, permittivity measurements of the crude oils and gas condensates were obtained at 25° C. using two multipoint resonant cavities. In certain embodiments, the permittivity measurements were obtained at two or more frequencies. These permittivity measurements can be related back to specific components of the hydrocarbons, such as the asphaltene content, the aromatic content, the xylene content, the toluene content, and the heptane content of the hydrocarbons. Certain embodiments of methods of geochemical characterization of the fluid hydrocarbons include obtaining permittivity values for different frequencies between 100 MHz and 20 GHz. Certain embodiments of methods of geochemical characterization of the fluid hydrocarbons include obtaining permittivity values for nine different frequencies between 170 MHz and 8.6 GHz. For example, the permittivity spectra can be related back to the asphaltene content, which is a function of the maturity of the source rock from where the hydrocarbons originated, and also the aromatic content, which is derived due to either thermochemical sulfate reduction or evaporative fractionation. In addition, at higher frequencies ranging from 2 GHz to 8.6 GHz, the permittivity spectra can be correlated with the xylenes and the toluene content of the produced fluids.

In the following description, numerous specific details are set forth in order to provide a thorough understanding of the various embodiments. In certain instances, well-known processes and methods may not be described in particular detail in order not to unnecessarily obscure the embodiments described here. In the following detailed description, reference is made to the accompanying drawings that form a part of this disclosure. The drawings may provide an illustration of some of the various embodiments in which the subject matter of the present disclosure may be practiced. The drawings may omit certain features or details in order to not obscure the embodiments described here. Other embodiments may be utilized, and logical changes may be made without departing from the scope of this disclosure.

The description may use the phrases "in some embodiments," "in various embodiments," "in an embodiment," or "in certain embodiments," which may each refer to one or more of the same or different embodiments. Furthermore, the terms "comprising," "including," "having," and the like, as used with respect to embodiments of the present disclosure, are synonymous.

Embodiments of the apparatuses and systems disclosed here include multipoint microwave resonant cavities designed to obtain more accurate permittivity values for low loss dielectric fluids, such as liquid hydrocarbons, and to reduce the loss of broadband. In certain embodiments, the permittivity values of the fluid hydrocarbons were obtained from microwave measurements at 25° C. using two multipoint resonant cavities. The low frequency cavity produced five resonant frequencies and the high frequency cavity produced four resonant frequencies.

The relative permittivity $\varepsilon$ for a low-loss dielectric fluid has real ($\varepsilon'$) and imaginary ($\varepsilon''$) parts that exhibit frequency dependence and is determined by:

$$\varepsilon(f,T) = \varepsilon'(f,T) - j\varepsilon''(f,T) \quad \text{(Equation 1)}$$

where f is the frequency, T is the temperature, $\varepsilon'$ is real part of the complex dielectric constant and j is the imaginary constant $\sqrt{(-1)}$. The imaginary part $\varepsilon''$ of the complex dielectric constant is given by:

$$\varepsilon''(f,T) = \varepsilon_d''(f,T) + \sigma_{DC}(T)/(2\pi f \varepsilon_0) \quad \text{(Equation 2)}$$

where $\varepsilon''$ is the sum of the dielectric losses ($\varepsilon_d$) and the conductive losses. $\sigma_{DC}$ is the direct current conductivity, and $\varepsilon_0$ is the permittivity of vacuum.

The polarization of a dielectric resulting from permanent dipole moments of molecules in polar fluids decays exponentially. Therefore, the imaginary part of the relative permittivity of polar fluids exhibits a rapid decay from exposure to the low frequencies. The rate of decay decreases depending on the conductivity and composition of the fluid. The decay reaches maxima at certain frequencies, and continues at a decreased pace until a limit value is reached. The frequencies at which the maxima occur are called the relaxation frequencies (unit is 1/time; for example, 1/sec). The inverse of a relaxation frequency is defined as relaxation time. Given the low conductivity of hydrocarbons, oil and gas condensate have lower relaxation frequencies and greater relaxation times as compared to water. In addition, the hydrocarbon component chemistry, which varies with temperature, affects the complex permittivity.

Embodiments disclosed here include a method for characterizing a geochemical property of a liquid hydrocarbon. One such method includes exposing a portion of the liquid hydrocarbon at a predetermined temperature to two or more microwave resonant cavities. Then, electromagnetic waves at microwave frequencies are provided from the microwave resonant cavities to elicit dielectric responses from the portion of the liquid hydrocarbon. In certain embodiments, the frequencies can range from the 100 MHz to the 20 GHz. These microwave frequencies can also range from 100 MHz to 10 GHz. In other embodiments, the microwave frequencies range from 170 MHz to 8.6 GHz. The dielectric responses from the portion of the liquid hydrocarbon in response to the electromagnetic waves at the microwave frequencies are measured and permittivity values are determined. These permittivity values are used to determine a geochemical property of the liquid hydrocarbon. The geochemical property can be one or more of saturates content, aromatics content, resins content, or asphaltenes content of the liquid hydrocarbon. The geochemical property can be toluene content or xylenes content of the liquid hydrocarbon. The geochemical property can be a ratio of the metal content associated with vanadium porphyrins or nickel porphyrins to the sulfur content present in the fluid. Each geochemical property has been previously calibrated with at least SARA and GC analyses.

Another embodiment includes methods for characterizing a geochemical property of a liquid hydrocarbon based on dielectric measurements at multiple frequencies at different temperatures. In one such method, a portion of the liquid hydrocarbon is exposed at a first predetermined temperature to a low frequency microwave resonant cavity and a high frequency microwave resonant cavity. Electromagnetic waves are provided at microwave frequencies from the low frequency microwave resonant cavity and the high frequency microwave resonant cavity to produce a set of dielectric responses from the portion of the liquid hydrocarbon, which are measured and stored. Subsequently, that portion of the liquid hydrocarbon is exposed at a second predetermined temperature in the low frequency microwave resonant cavity. Then, electromagnetic waves at this set of microwave frequencies as provided from the low frequency microwave resonant cavity elicit a set of dielectric responses from the portion of the liquid hydrocarbon, which are measured and stored. Finally, that portion of the liquid hydrocarbon is exposed at a third predetermined temperature in the high frequency microwave resonant cavity. Electromagnetic waves at a next set of microwave frequencies as provided from the high frequency microwave resonant cavity elicit a set of dielectric responses from the portion of the liquid hydrocarbon, which are measured and stored. Using at least these four sets of dielectric responses, permittivity values are calculated that are used to determine a geochemical property of the liquid hydrocarbon.

A multipoint resonant cavity may give four to five resonant frequencies in a broad spectrum. Using two similar size cavities will allow to fill in between the discrete frequencies. Using two cavities of different sizes increases the frequency spectrum range. The larger the cavity, the lower the frequency it provides and vice-versa. In certain embodiments, the first set of microwave frequencies can range from 100 MHz to 20 GHz. These microwave frequencies can also range from 100 MHz to 10 GHz. In certain embodiments, the first set of microwave frequencies can range from 170 MHz to 8.6 GHz. In certain embodiments, the second set of two or more microwave frequencies from the low frequency microwave resonant cavity can range from 100 MHz to 2.3

GHz. In certain embodiments, the second set of two or more microwave frequencies from the low frequency microwave resonant cavity can range from 170 MHz to 2.3 GHz. The third set of two or more microwave frequencies from the high frequency microwave resonant cavity range from 1.3 GHz to 20 GHz. The third set of two or more microwave frequencies from the high frequency microwave resonant cavity range from 1.3 GHz to 8.6 GHz. Measuring hydrocarbons at temperatures greater than 40° C. has the disadvantage of being exposed to increased evaporation of hydrocarbons with $C_1$ to $C_7$ chain length. This leads to changes in the electrical properties as detected by the system. Moreover, these hydrocarbons do not store heat well. The temperature has to be measured immediately (in 5 to 8 seconds) before the temperature decreases. In certain embodiments, the samples are analyzed under a temperature controlled environment. In certain embodiments, the first set of measurements are taken at 25° C., and the second set at 25.5° C. from the low frequency microwave resonant cavity and at 26° C. from the high frequency microwave resonant cavity. Measuring dielectric measurements at two temperatures reduces the fluctuations based on variations in the temperature measurements. Preliminary results show that the dielectric measurements are less sensitive at temperature ranges from about 20° C. to about 50° C. At about 100° C., the dielectric measurements are comparatively more sensitive to the temperature variations, which could be the result of evaporations of certain $C_1$ to $C_7$ hydrocarbons. The geochemical property can be one or more of saturates content, aromatics content, resins content or asphaltenes content of the liquid hydrocarbon. The geochemical property can be toluene content or xylene content of the liquid hydrocarbon or both. The geochemical property can be content of vanadium porphyrins or nickel porphyrins or sulfur. The geochemical property can be a ratio of the metal content associated with vanadium porphyrins or nickel porphyrins to the sulfur content present in the fluid.

Microwave cavity measurements are conducted with either multipoint re-entrant coaxial resonant cavities that give permittivity values for a finite number of frequencies or with individual frequency cavities. Frequencies are typically in the GHz range. In certain embodiments, the frequencies are set by the cavity geometry (size and shape) and by the type of electromagnetic mode that propagates in such cavity. Embodiments of the apparatus include a multipoint re-entrant cavity configured to receive a vial containing a sample. Embodiments of the apparatus include a multipoint re-entrant cavity, whose resonance can be modeled by analytical or numerical methods as demonstrated here. The cavities can also be cubes or cuboids in shape. In an embodiment, the apparatus is a cylindrical cavity configured to accept a vial containing the liquid hydrocarbon sample and function at frequencies as low as 100 MHz. In an embodiment, the cavity has a coaxial opening in the top that does not extend all the way to the bottom. In certain embodiments, the cavity has a removable lid for placing and removing samples, a sample holder, a resonator mechanism for adjusting the resonance frequency of the cavity, an output dielectric response detector, and one or more fastening mechanisms for securely holding the lid to the base during operation. Sources of microwaves are communicatively connected to the cavity, and detectors are provided on the sides of the cavity or as mounted on the cavity lid. The external microwave sources and detectors are controlled by a computer using an appropriate software. Vials containing test samples can be in the form of rectangular solids or cylinders, with the dimensions suitably appropriate to the height and diameter of the cavity. In certain embodiments, the cavity has inlet and outlet ports for gas such that the cavity could be pressurized and put under an artificial atmosphere. The apparatus includes components to adjust the frequency of the microwaves delivered to the sample. The apparatus can include shielding components to protect the operators from the electromagnetic radiation.

Certain embodiments of the cavities are made of aluminum. In an embodiment, the cavity is partially filled with polytetrafluoroethylene compounds to further lower the frequency delivered to the sample. In certain embodiments, the polytetrafluoroethylene compound is Teflon®. In an embodiment, the low frequency cavity has a diameter of about 59.6 millimeters (mm) and a length of about 250 mm. This cavity is configured to hold a vial with an internal diameter of 13 mm. To deliver frequencies of about 100 MHz, the length of the cavity can be increased. In certain embodiments, the cavities can be made of more conductive materials, such as silver, copper, or gold, to minimize the losses suffered at lower frequencies. Certain embodiments include a silver bath in the inner surfaces of a large cavity to capture resonant modes at lower frequencies.

In certain embodiments, the high frequency cavity is made of aluminum. Its dimensions can include an internal diameter of about 40 mm and a length of about 97.8 mm. This cavity is configured to hold a vial with an internal diameter of about 8 mm. All cavities are well characterized in the modeling system to achieve accurate values with the inversion algorithm.

Certain embodiments involve the use of a multipoint re-entrant microwave cavity, and not a photonic band gap cavity. In certain embodiment, a cavity can be a cylinder with no periodic arrangement of materials having dissimilar permittivity. Unlike other technologies, where different cavities are used for different frequencies, apparatuses disclosed here are configured to provide for the multifrequency features and can also include a cavity with an opening in the middle. An example of a multipoint re-entrant microwave cavity is an aluminum multipoint cavity with a quartz vial inserted from the top. Certain embodiments of the methods of measuring the dielectric responses include operating the cavities at very specific temperatures. A method of measuring the dielectric responses includes the steps of separating a portion of the liquid hydrocarbon from the production fluid containing the liquid hydrocarbon and brine, and measuring temperature of that portion of the liquid hydrocarbon. If the temperature is steady, dielectric responses of that portion of the liquid hydrocarbon are collected and analyzed. If temperature is not steady, a heat source like a hot plate or portable mini oven is used to reach steady temperatures. All fluids under evaluation are maintained at about the same temperatures.

The hydrocarbon sample can be open to the atmosphere or in a sealed container. The container is be made of a material, whose dielectric properties remain unchanged within the desired temperature range. For example, quartz or sapphire are appropriate materials. Their dielectric properties are constant up to about 1200° C. In certain embodiments, the frequencies range from 100 MHz to 10 GHz.

Certain embodiments of the system described here can be deployed at the site where the hydrocarbons are present. For example, the production fluids can be measured at one or more sampling sites in an oil-productive geologic region. In another example, subsequent to an oil spill, samples from the contaminated region can be analyzed by marine vessel-based or shore-based systems using the devices, including the multipoint resonant cavities, and methods described here. These analyses can facilitate the evaluation of the extent of contamination resulting from the spill. The size of the samples and the design of the cavities have to be adjusted to provide for the presence of the saline water in the hydrocarbon sample. In another example, the hydrocarbon concentrations of samples from a land or water oil spill can be measured as part of a monitoring program. The effect of remediation strategies applied to a spill can also be evaluated by using the methods and systems described here to assess a decline of hydrocarbon concentrations in the oil spill environment.

Example 1

FIG. 1 is a diagram illustrating a system, according to an embodiment. The system 100 includes two ITACA multipoint resonant cavities—a low frequency cavity 102 and a high frequency cavity 104. The low frequency cavity 102 is a large multipoint cavity for the lower frequencies. The high frequency cavity 104 is a small multipoint cavity for higher frequencies. Both of the cavities used here were developed at the Institute of Information and Communication Technologies (ITACA) of the Universitat Politècnica de València, Spain. The system further includes a Rohde & Schwarz R&S®ZVA50 vector network analyzer (VNA) 106 (available from Rohde & Schwarz GmbH & Co KG headquartered in Munich, Germany). The system also includes two Gore VNA cables 108 and 110, a computer 112 with the cavities software, thermometers 114 (calibrated by National Institute of Standards and Technology services), vials 116, vial holders or stands 118, and hot plates 120. The VNA was first calibrated using an Agilent Technologies 85052B calibration kit. The cavities were then connected to the VNA with the two VNA cables. The measurements were taken with empty vials on both cavities and measurements during resonant modes were saved. Hydrocarbon samples were poured in vials (10 milliliters (mL) and 4 mL), and vials were placed on the hot plate until a predetermined temperature was reached. The vials were then placed in their respective cavity and measurements were taken immediately after predetermined temperature was reached. The measurements were communicated to and stored by a computer with the ITACA software. The mode matching method using the $TE_{0np}$ modes to calculate the generalized impedance matrix, as presented by ITACA software, was used to compute the permittivity values and quality factors from the resonant frequency values of both the empty vials and vials filled with fluid hydrocarbons. The TE mode is the waveguide mode that is dependent upon the transverse electric waves and the integers m, n, and p in the subscript denote the number of half-wave variations in the x, y, and z direction, respectively. In the $TE_{0np}$ mode, m=0. Initially both geochemical analysis and multipoint microwave cavity measurements were performed to obtain the permittivity values as a function of frequency and temperature. In order to include the uncertainty from temperature variations, measurements at each cavity were taken at two different temperatures. The first set of measurements was taken at 25° C. and the second set at 25.5° C. for the large cavity and 26° C. for the small cavity.

Example 2

Three samples were selected for analysis using methods disclosed here. These samples also have different thermogenic maturity of the source generating the hydrocarbon. The first sample, Crude 1, was a medium oil with an API of 28.2. The second sample, Crude 2, was a light oil with an API of 39.0. The third sample, Condensate, was a condensate of an API of 45.8. Geochemical analyses include SARA analysis to determine the bulk chemistry, gas chromatography to determine hydrocarbon component chemistry, and GCMS to determine biomarker chemistry to determine maturity and source of the hydrocarbons. Biomarkers include a variety of hydrocarbons, including alkanes, polycyclic aliphatics, and polycyclic aromatic hydrocarbons. The saturates content, aromatics content, resins content, and asphaltenes content of the three samples is shown in Table 1, where the basic geochemical properties of a hydrocarbon sample are expressed as a percentage of its composition: saturates, aromatics, resins and asphaltenes.

TABLE 1

| Hydrocarbon | Saturate (%) | Aromatics (%) | Resins (%) | Asphaltenes (%) |
|---|---|---|---|---|
| Crude 1 | 29.27 | 26.03 | 17.31 | 8.84 |
| Crude 2 | 43.73 | 18.67 | 9.02 | 3.63 |
| Condensate | 65.92 | 10.83 | 5.02 | 0.13 |

Figure 2A:
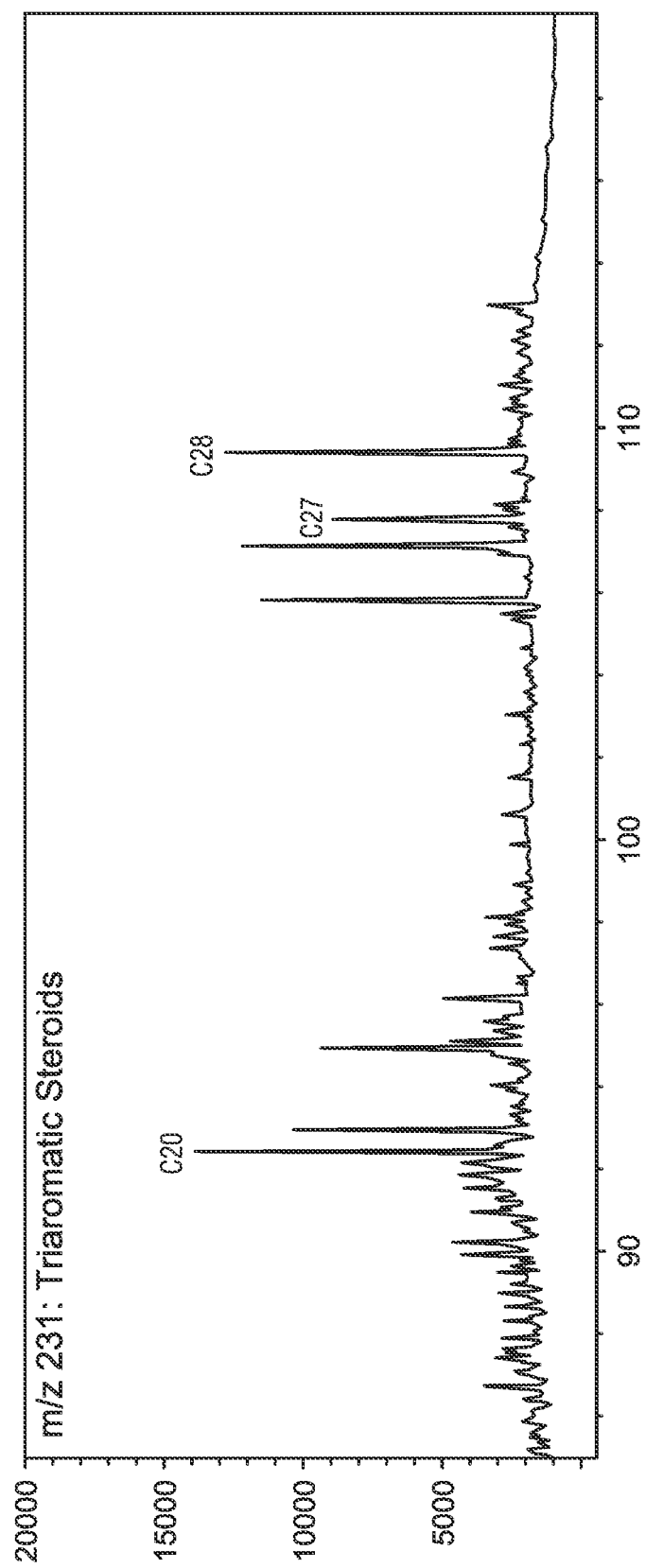
Figure 2B:
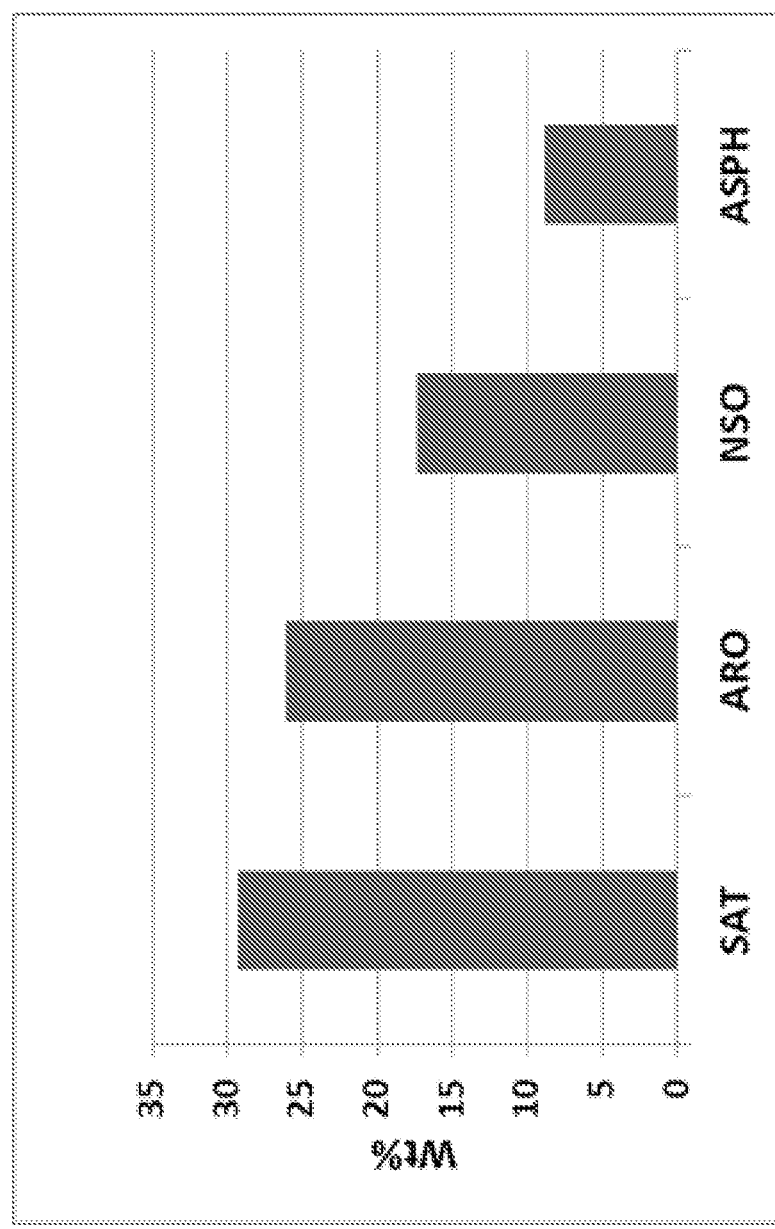
FIGS. 2B, 2D, and 2F are the bar graphs showing the relative SARA components of the three samples, respectively.
Figure 2C:
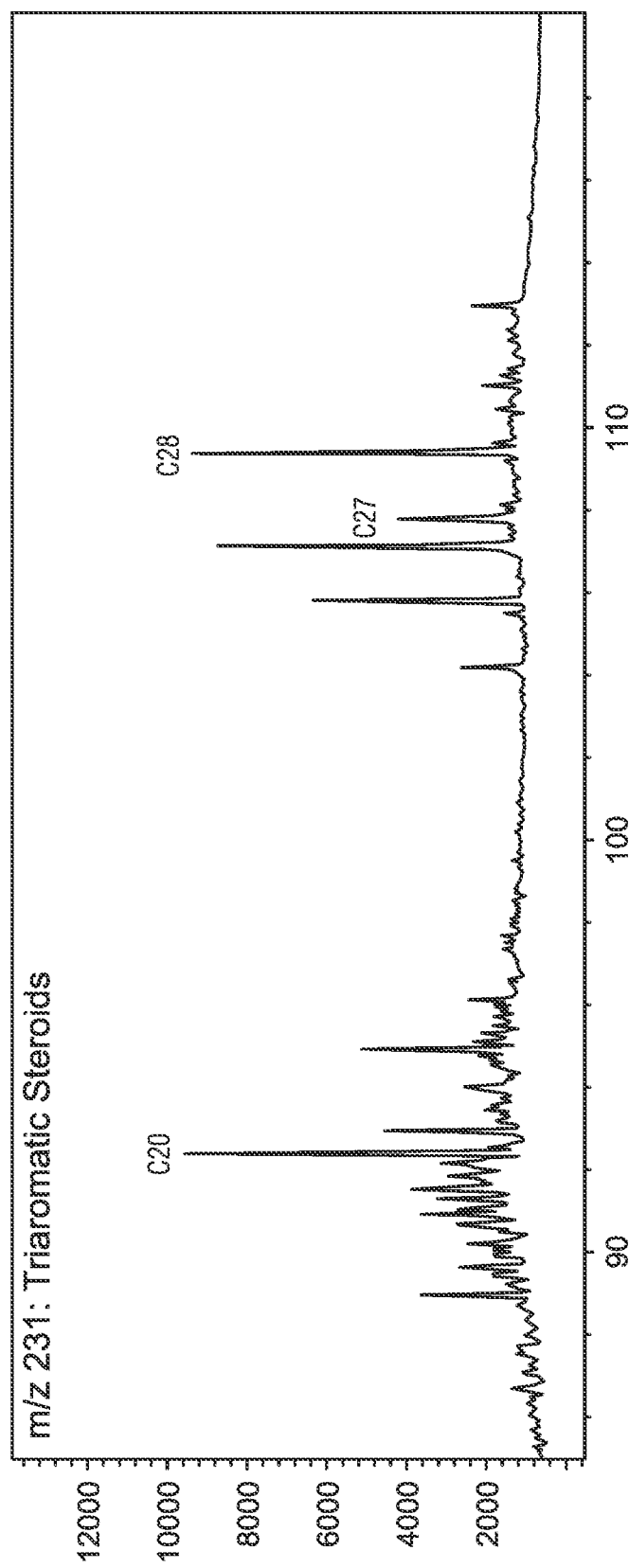
Figure 2D:
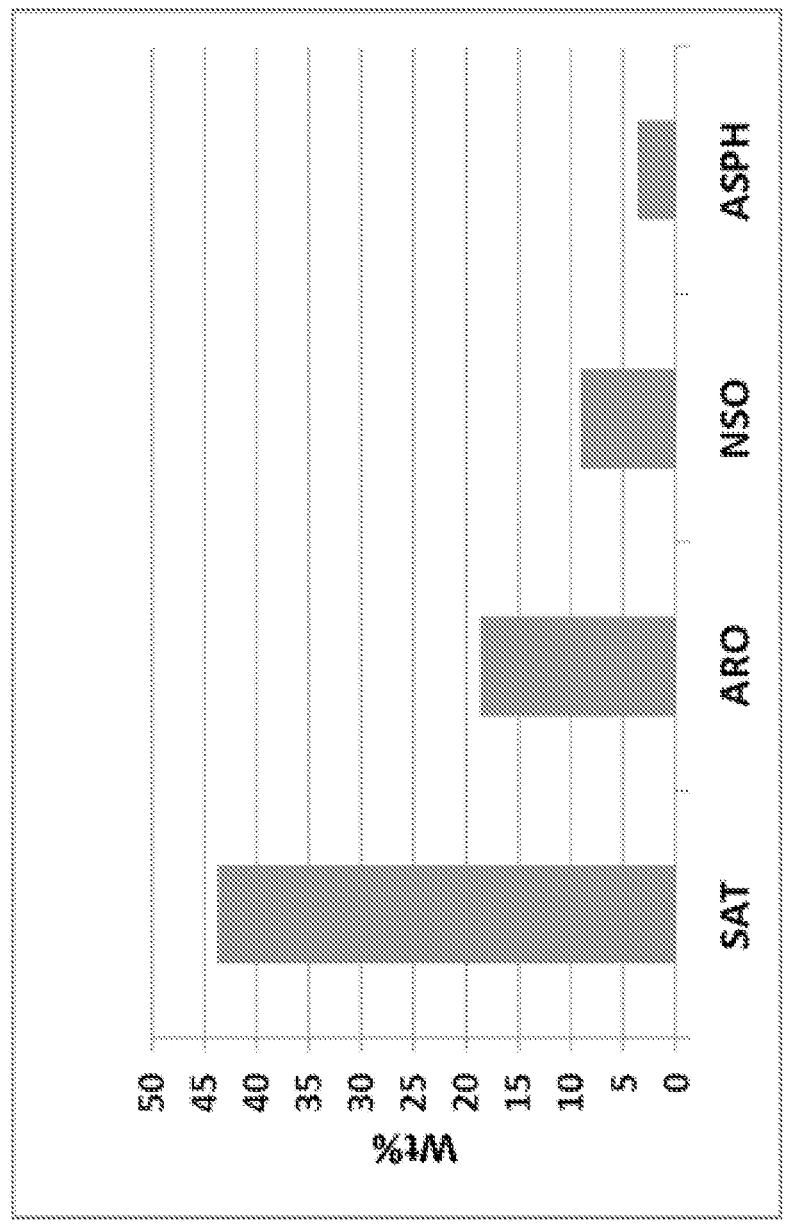
Figure 2E:
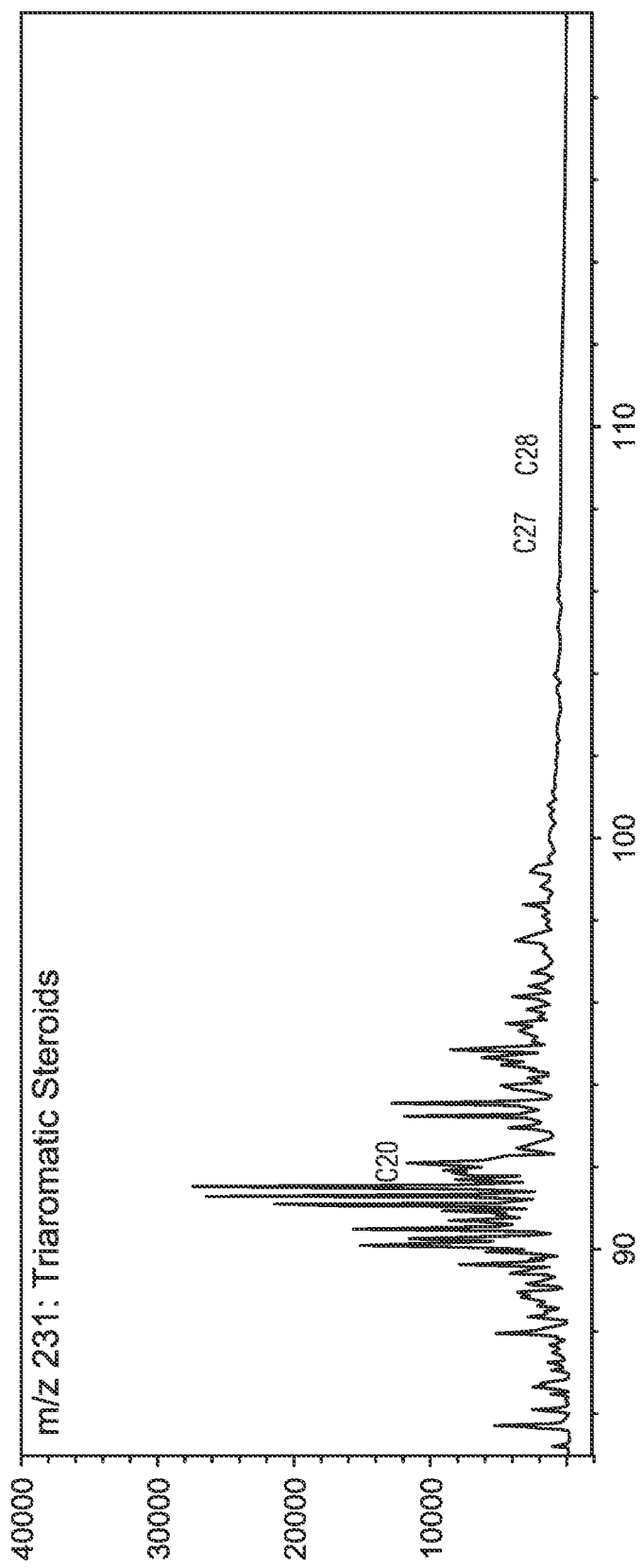
Figure 2F:
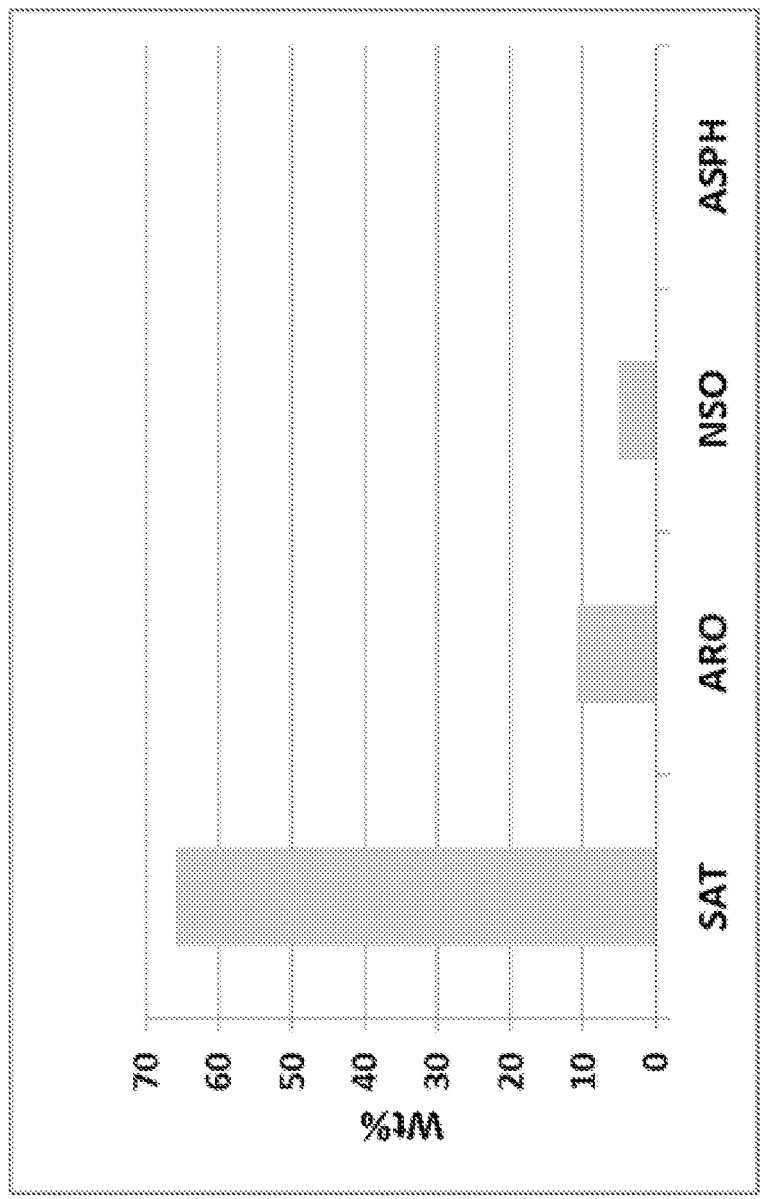

Biomarker analysis of the three samples was performed using GCMS. Biomarker analysis is conducted on the saturate and aromatic fractions, which are separated from the resins and asphaltenes using chromatography methods. The GCMS system equipped for biomarker analysis consists of a column (60 meters in length), which is maintained at a certain temperature using a programmable temperature controller. This controller allows one to set a final temperature to be attained and a ramp rate dictating how fast this final temperature should be attained from the start temperature of the sample. The carrier gas flow rate is designed to elute the biomarker isomers from the column according to their differences in retention time, and mass to charge ratio. The aromatic steroids frequently detected in crude oils range from $C_{20}$ to $C_{30}$ homologs. The m/z 231 chromatogram peaks are obtained by analysis of that portion of the sample having a mass-to-charge ratio (m/z) of 231 and represent the tri-aromatic $C_{20}$ steroids in the hydrocarbon samples. The mass-to-charge ratio (m/z) is a dimensionless quantity obtained by dividing the ratio of the mass of an ion in atomic mass units by its charge number. The distinguishable tri-aromatic steroids in most oil samples include TAS-cholestanes ($C_{26}$), TAS-ergostanes ($C_{27}$), and TAS-stigmastanes ($C_{28}$). When comparing this ratio to the changing saturate/aromatic fraction of the oils, there is a direct correlation between the $C_{20}$ to $C_{27}$ biomarker ratio and the API and saturate/aromatic ratio of the sample. FIGS. 2A, 2C, and 2E are the mass spectrums obtained for the three samples following GCMS analysis, while FIGS. 2B, 2D, and 2F are the bar graphs showing the relative SARA components of the three samples, respectively. There was a steady decline in the amount of $C_{27}$ tri-aromatic steroids relative to $C_{20}$ tri-aromatic steroids, as shown in FIGS. 2A, 2C, and 2E. This decline corresponds to the steady increase in saturate to aromatic ratio observed in the SARA of Sample 1 (1.12), Sample 2 (2.34), and Sample 3 (6.08), as determined from Table 1 and FIGS. 2B, 2D, and 2F. These observations correspond to the increasing thermogenic maturity of the source generating the hydrocarbon. This steady decline in the amount of $C_{27}$ tri-aromatic steroids relative to $C_{20}$ tri-aromatic steroids, as shown in FIGS. 2A, 2C, and 2E, correlates with the declining resin and asphaltene concentrations shown in FIGS. 2B, 2D, and 2F. Other biomarkers can be used from both the saturate and aromatic fractions to check the validity of any ratios computed using the $C_{27}$.

However, not all biomarkers are suitable. For example, to the left of $C_{27}$ peak is the $C_{28}$ TAS stigmastane peak that illustrates the problem of using this isomer peak for determining maturity. The ratio of C20 to C28 does not change from the oil of API 28.2 (FIG. 2A) to that of the oil of API 39 (FIG. 2C), indicating that this biomarker ratio is not reflective of the change in maturity.

As measured at 60° F., from the least to the most mature oil, Crude 1 sample at an API of 28.2 corresponds to a medium grade oil (density of 886 kilogram per cubic meter ($kg/m^3$)), Crude 2 sample at 39.0 corresponds to a light oil (density of 829 $kg/m^3$) and Condensate sample at 45.8 corresponds to a condensate (density of 801 $kg/m^3$). Another geochemical property that was evaluated was the ratio of the metal content associated with vanadium porphyrins or nickel porphyrins to the sulfur content present in the fluid. Crude 1 sample had vanadium porphyrins (V) present at 23 parts per million by weight (ppm), nickel porphyrins (Ni) at 9.7 ppm, and sulfur at 2.39 weight percent (wt %). Crude 2 sample had vanadium porphyrins present at 1.1 ppm, nickel porphyrins at <1 ppm, and sulfur at 0.68 wt %. Sample 3 had vanadium porphyrins present at <0.4 ppm, nickel porphyrins at <1 ppm, and sulfur at 0.01 wt %. The corresponding declining metal content associated with nickel and vanadium porphyrins compared to the sulfur content in the oils correlates to the declining conductivity σ measured in picosiemens per meter (pS/m) for each of the samples and presented in Table 2.

TABLE 2

| Hydrocarbon | API | V (ppm) | Ni (ppm) | S (wt %) | σ (pS/m) |
| --- | --- | --- | --- | --- | --- |
| Crude 1 | 28.2 | 23 | 9.7 | 2.39 | 71640 |
| Crude 2 | 39.0 | 1.1 | <1 | 0.68 | 11253 |
| Condensate | 45.8 | <0.4 | <1 | 0.01 | 7 |

Figure 3A:
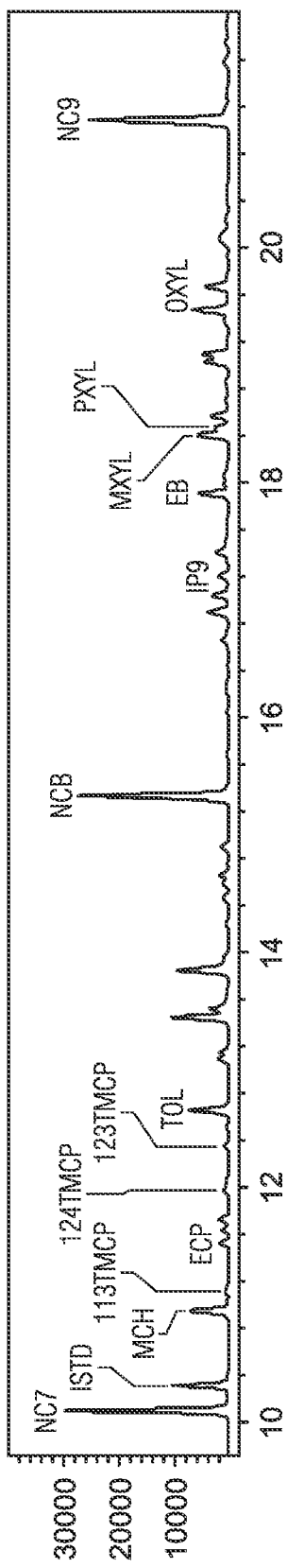
FIGS. 3A, 3B, and 3C are GC chromatograms of the samples showing the various components.
Figure 3B:
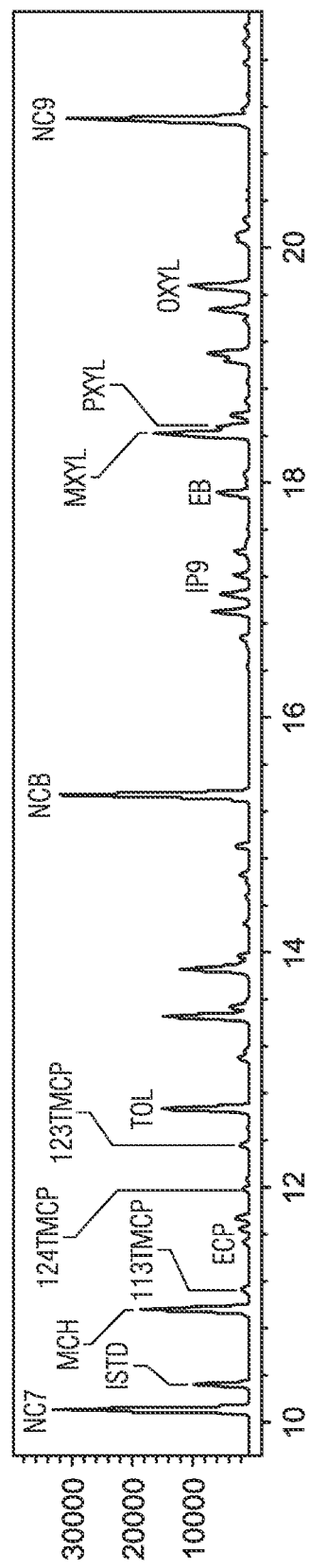
Figure 3C:
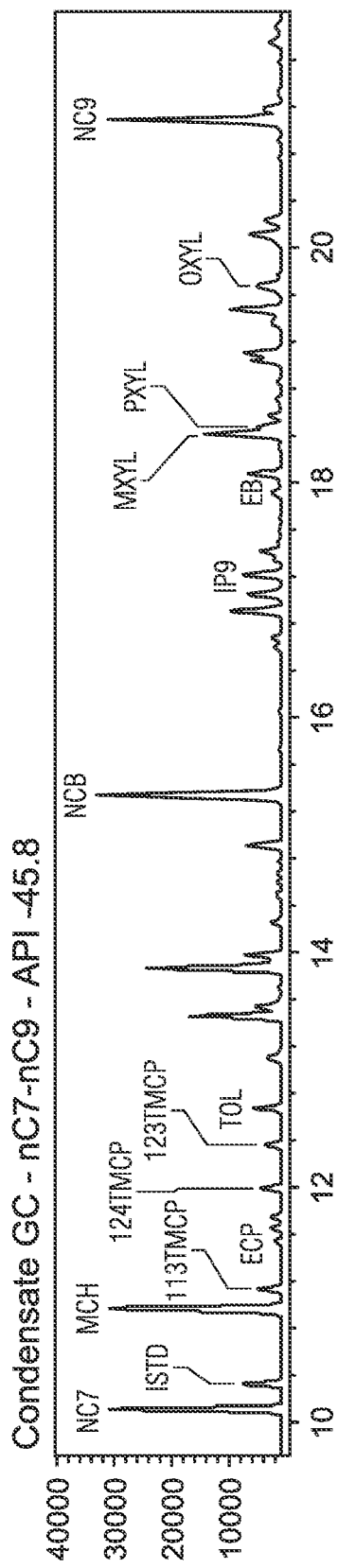

The bulk aromatic values of the samples vary in molecular composition, which also influence the conductivity and the dielectric losses. The observed variability could be linked to both differences in the source of the hydrocarbons and possible alteration in composition due to either thermochemical sulfate reduction or evaporative fractionation or both. Thermochemical sulfate reduction involves the reduction of sulfate to hydrogen sulfide by a reaction with $C_1$ to $C_7$ hydrocarbons in connection with anhydrite at temperatures greater than 150° C. The increase in aromatics could be related to the decomposition of n-alkanes during thermochemical sulfate reduction of light oils and condensates because of their increased saturate reactivity. This increase in m-xylene (peaks in FIGS. 3A-3C identified as M-XYL) and toluene (peaks in FIGS. 3A-3C identified as TOL) relative to the normal heptane (peaks in FIGS. 3A-3C identified as NC7) and methylcyclohexane (peaks in FIGS. 3A-3C identified as MCH) was confirmed by gas chromatography analysis. FIGS. 3A, 3B, and 3C are GC chromatograms of the samples showing the various components. FIG. 3C shows an abnormal increase in MCH (peak at t=10.9) and m-xylene (peak at t=18.4) compared to the $nC_7$ (peak at t=10.1) in the gas chromatograph of the gas condensate. The liquid hydrocarbon can be characterized by using one or more of the following properties: heptane content, toluene content, or xylenes content, or toluene to heptane ratio, or xylenes to heptane ratio of the liquid hydrocarbon.

Figure 4:
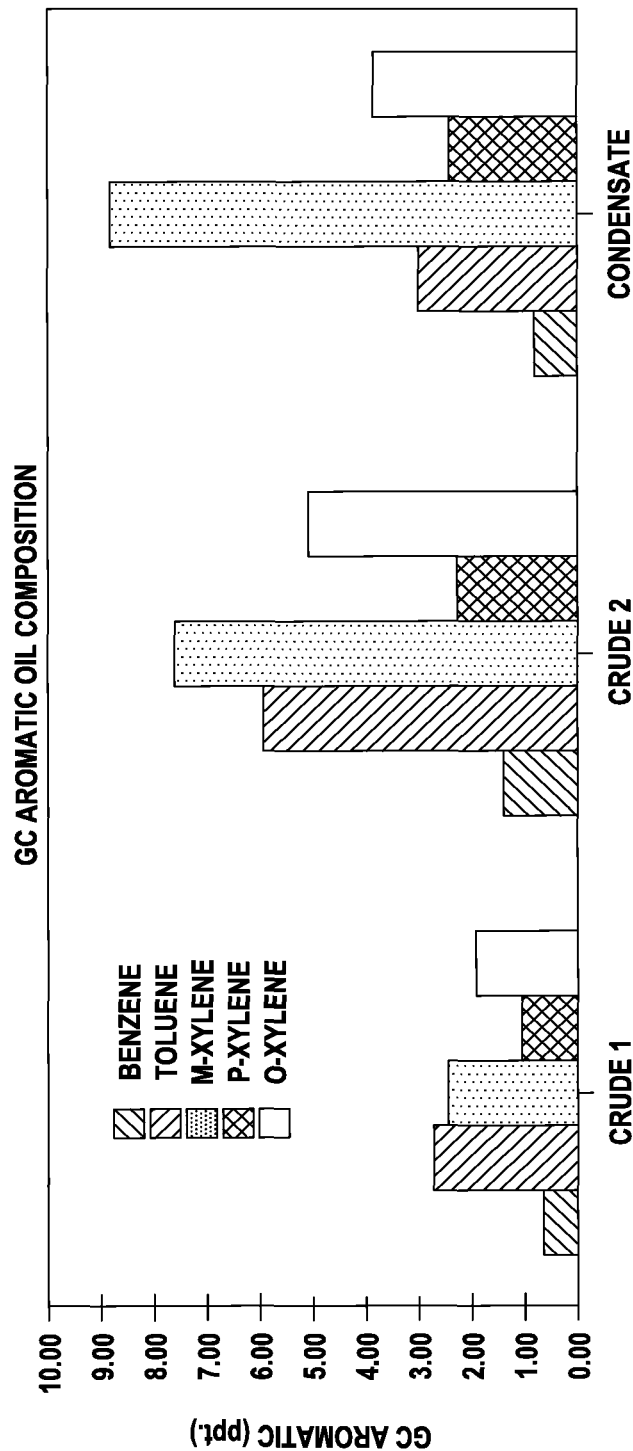
FIG. 4 is a graphical representation of the amounts of benzene, toluene, m-xylene, p-xylene, and o-xylene present in the three samples.

FIG. 4 is a bar graph representation of the amounts of benzene, toluene, m-xylene, p-xylene, and o-xylene present in the three samples. The increases in toluene and all xylenes in Crude 2 and the condensate are greater for the maturity compared to the values observed for Crude 1. Evaporative fractionation results from increasing gas pressure in the reservoir that promotes a change in the vapor-liquid equilibria of the lighter n-alkanes ($C_1$ to $C_7$). The resulting conversion of the n-alkanes to gaseous forms causes the loss of reservoir accumulation.

Figure 5:
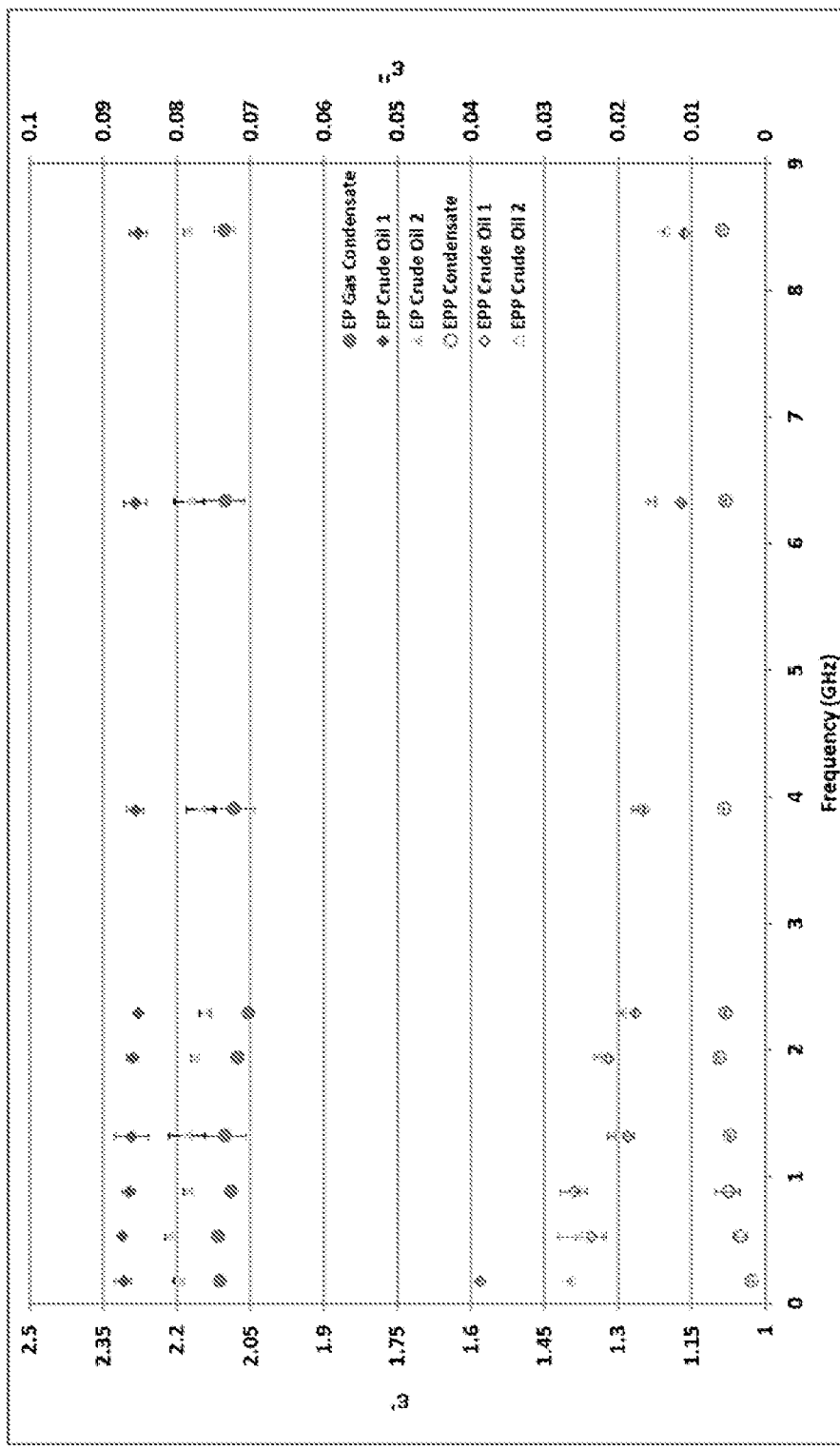
FIG. 5 is a graphical representation of the dielectric spectra for liquid hydrocarbons at 25 degrees Celsius (° C.), obtained from the permittivity measurements at 25° C. and their respective uncertainty bars, according to an embodiment.

The same three samples were subject to permittivity measurements at two different temperatures using two state of the art multipoint resonant cavities. Permittivity values were obtained for nine different frequencies between 170 MHz and 8.6 GHz. The low frequency cavity was utilized at five resonant frequencies and the high frequency cavity at four resonant frequencies. The first set of measurements was taken at 25° C. and the second set at 25.5° C. for the large cavity and 26° C. for the small volume cavity. FIG. 5 is a graphical representation of the dielectric spectra for liquid hydrocarbons at about 25° C., obtained from the permittivity measurements at both sets of temperatures and their respective uncertainty bars. The values given are an average of all the values at the nearby temperatures to account for the slight variations in the temperature. The filled markers correspond to the real part of the relative permittivity (ε', left axes) and the empty markers correspond to the imaginary part of the relative permittivity (ε", right axes). Crude 1 is given by the green-diamond-shaped markers, Crude 2 by the orange-triangle-shaped markers and the Gas Condensate by the red-circle-shaped markers. The black error bars at each marker represent the general combined uncertainty (k=2) given by the measurements sets at the different temperatures. The real part of the permittivity, ε', shows values as previously reported. Also, it exhibits a trend that correlates with API gravity (density) and asphaltene content, as shown in Table 2. The results from these frequency measurements showed the dielectric losses measured correspond to a change in conductivity of the oils ranging from 28 API to 46 API. The changes in API and corresponding conductivities are the result of differences in asphaltene content that changes with maturity. As a result, the dielectric losses can be used to determine the API, possibly the maturity and thus the quality of hydrocarbon recovered during well production. Crude 1 has the greatest density, greatest asphaltene content, and greatest real relative permittivity, followed immediately by Crude 2 and then by the gas condensate. Thus, if accurate permittivity measurements are made at well-site, then density or SARA content or both can be estimated. By monitoring the changes in the permittivity measurements, changes in the density or SARA content or both can be monitored over time at the same location or at different locations in the hydrocarbon-productive geologic region.

Based on art in the field, one would expect the uncertainty in the measurements to increase for the fluids with lower density. However, the differences in density do not seem to be large enough to produce a noticeable effect on the measured uncertainty. The imaginary part of the relative permittivity is related to the losses the electromagnetic waves experience while propagating in each fluid. So, ε" data from previous studies show significant uncertainty, making comparisons difficult. But here, from equation (2) and Table 2, the conductivity losses for Crude 1 become less influential for frequencies greater than 1.28 MHz, for Crude greater than 200 kHz and for gas condensate greater than 200 Hz. At these frequencies, the dielectric loss term is unmasked and dielectric relaxation processes can be observed. The frequencies are determined by the cavities. In this example, the cavities were designed to give several (discrete) frequencies in a broad spectrum. The design of the cavities can be modified to include more discrete points between frequencies. In certain embodiments, where the ε" (EPP) data at higher frequencies correspond to other information about the geochemical components, the cavities can be designed to have an arrangement of sizes to provide for a broader swept spectrum. As shown in FIG. 5, the behavior of the imaginary part (EPP) of the relative permittivity for Crude 1 and Crude 2 follows a similar trend to that observed in literature of polar fluids. From these trends, relaxation frequencies in the low GHz range can be inferred for both crudes, consistent with previous studies. In addition, EPP for gas condensate has lower values than those of crude, in the $10^{-3}$ range, and shows an increasing behavior at low frequencies that starts to decay slowly at higher frequencies. This is indicative of a larger relaxation frequency and a shorter relaxation time than crude oil. At higher frequencies in FIG. 5, the EPP or the loss term for Crude 2 exhibits greater values than the more conductive Crude 1. This behavior may be because at higher frequencies, the conductive losses are negligible. Thus, the composition of the hydrocarbon fluid affects the loss term.

Figure 6:
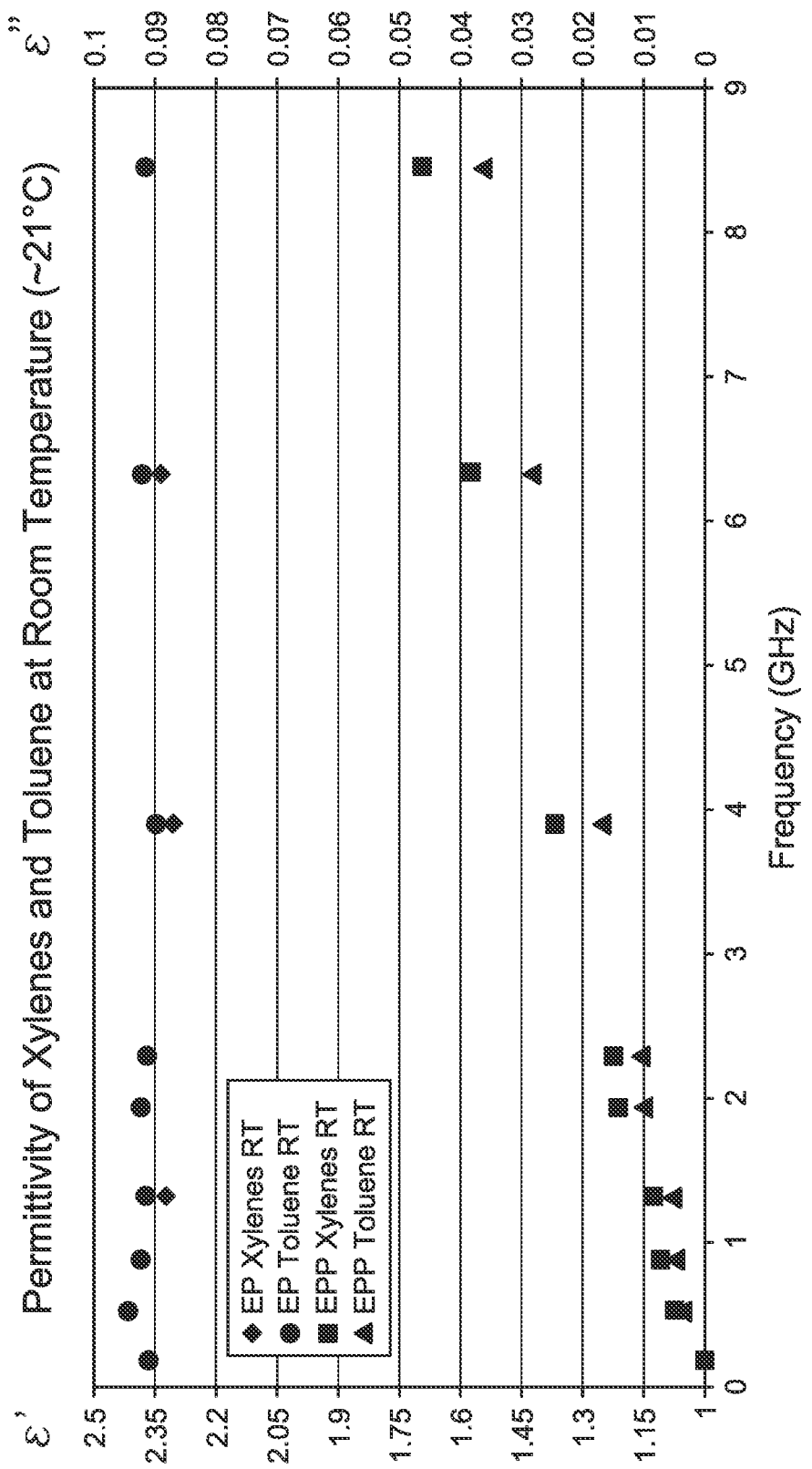
FIG. 6 is a graphical representation of the measured permittivity spectrum of xylenes and toluene at 25° C.

The toluene and xylenes content in Crude 2 and the gas condensate are significantly greater than the toluene and xylenes content in Crude 1, see FIG. 4. FIG. 6 is a graphical representation of the measured permittivity spectrum of xylenes and toluene at room temperature. As shown in FIG. 6, the measured loss term (EPP) for xylenes and toluene increases in the frequency range of the cavities. This explains the slower decay in the loss term of Crude 2 and gas condensate. The increase in these two components could be the result of either thermochemical sulfate reduction or evaporative fractionation. These losses behavior exhibited by both toluene and xylenes explains the unusual microwave losses behavior that changed at higher frequency in FIG. 5. The more conductive oil (Crude 1) started to exhibit less losses than the less conductive oil (Crude 2). Despite Crude 1 being more conductive, it had less content of toluene and xylenes than Crude 2. Thus, this crossover in the microwave losses provides predictive information about the toluene and xylenes content.

An interdisciplinary approach has been taken to understand permittivity measurements of hydrocarbons. The permittivity values obtained are strongly correlated to the geological processes and geochemistry of the hydrocarbon samples. Geochemical analysis and permittivity measurements were performed on crude oils and gas condensate at 25° C. for frequencies between 170 MHz and 8.6 GHz. Multipoint re-entrant coaxial cavities were used for their accuracy and low uncertainty. Results show that the real part of the relative permittivity is proportional to density and asphaltene content of the liquid hydrocarbons. The imaginary part of the relative permittivity of Crude 2 becomes larger than that of the more conductive Crude 1. Given that the loss term for toluene and xylenes increases at higher frequencies, this behavior could be explained geochemically by the toluene and xylenes content, which are significantly greater in Crude 2 than in Crude 1. Thus, by determining the permittivity values at different intervals during production, one can determine certain geochemical properties of the hydrocarbon fluid and assess the changes occurring during production.

Example 3

Figure 7A:
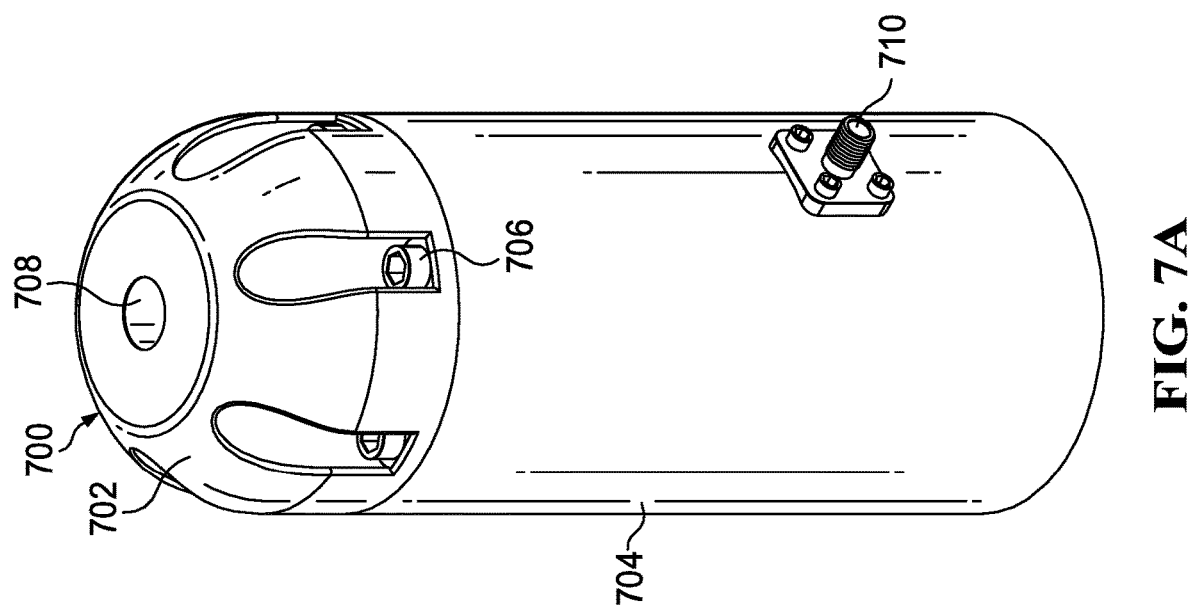
FIGS. 7A-7C are diagrammatic representations of an apparatus, according to an embodiment.
Figure 7C:
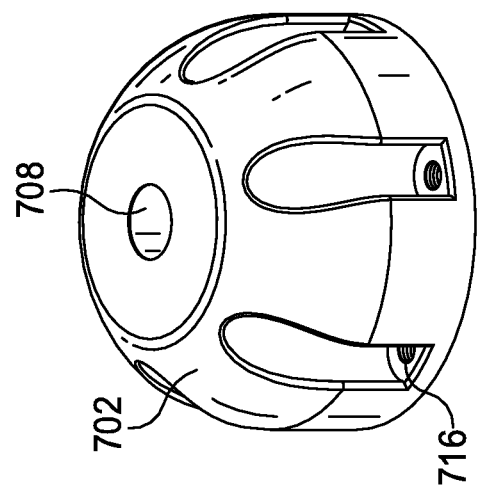
Figure 7B:
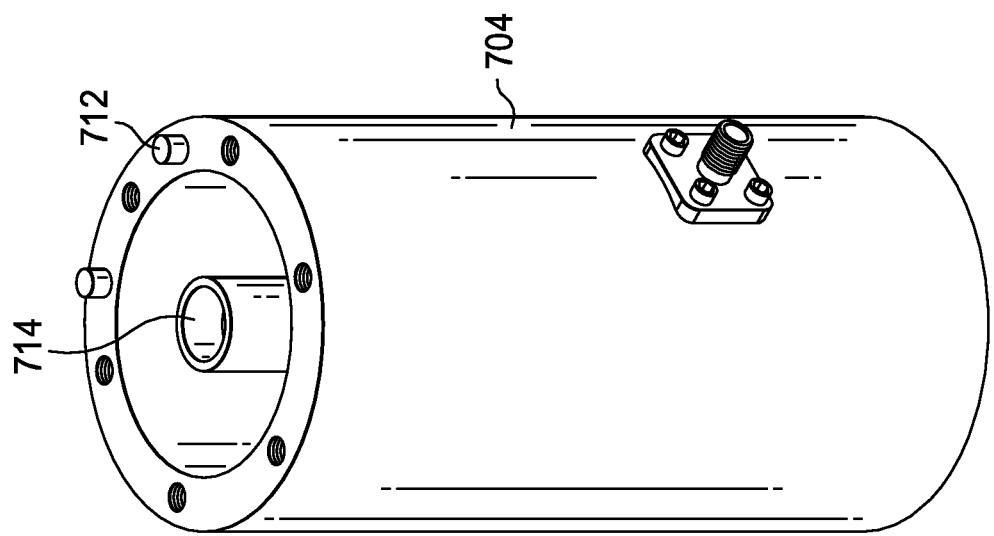

FIGS. 7A-7C are diagrammatic representations of an apparatus, according to an embodiment. As shown in FIG. 7A, the apparatus 700 is a cylindrical cavity configured to accept a vial containing the liquid hydrocarbon sample and function at frequencies as low as 100 MHz. The cavity 700 has two components, a lid 702 and a base 704. The lid 702 and base 704 are secured together by a series of nuts and bolts 706 serving as the fastening mechanism. The lid 702 has a coaxial opening 708 on the top that does not extend all the way to the bottom of the cavity. The cavity 700 is also equipped with port 710 that communicatively connects the cavity to the dielectric response detection system. Not shown, but also provided here is a port that communicatively connects the cavity to the source of microwaves. The external microwave sources and dielectric response detectors are controlled by a computer, running appropriate software. FIG. 7B and FIG. 7C are diagrammatic representations of the base 704 and the lid 702 respectively, when separated from each other. As shown in FIG. 7B, the base 704 has slots 712 to receive suitable fastening mechanisms, such as bolts. The base 704 also has a station 714 to receive a sample holder such as vial. This station 714 is designed to receive a cylindrical vial. As shown in FIG. 7C, the lid 702 has a coaxial opening 708 on the top and complementary slots 716 to receive suitable fastening mechanisms, such as bolts, to secure the lid 702 to the base 704 via slots 712.

Ranges may be expressed in this disclosure as from about one particular value and to about another particular value. When such a range is expressed, it is to be understood that the interval encompasses each intervening value between the upper limit and the lower limit as well as the upper limit and the lower limit and includes smaller ranges of the interval subject to any specific exclusion provided. Embodiments can include any and all combinations within said range.

Where a method with two or more defined steps is recited or referenced here, the defined steps can be carried out in any order or simultaneously except where the context excludes that possibility. Elements and materials may be substituted for those illustrated and described here. The parts and processes may be reversed or omitted and certain features of the embodiments may be utilized independently. The various embodiments are intended to be illustrative and not limiting. As a result, it will be apparent for those skilled in the art that the illustrative embodiments described are only examples and that various modifications can be made within the scope of the disclosure as defined in the appended claims.

What is claimed is:
1. A method for characterizing a geochemical property of a liquid hydrocarbon, the method comprising:
exposing a portion of a liquid hydrocarbon at a first plurality of predetermined temperatures in a first microwave resonant cavity to electromagnetic waves at a first set of two or more microwave frequencies to elicit a first set of two or more dielectric responses from the portion of the liquid hydrocarbon;
measuring the first set of two or more dielectric responses from the portion of the liquid hydrocarbon in response to the electromagnetic waves at the first set of two or more microwave frequencies;
exposing the portion of the liquid hydrocarbon at a second plurality of predetermined temperatures in a second microwave resonant cavity to electromagnetic waves at a second set of two or more microwave frequencies to elicit a second set of two or more dielectric responses from the portion of the liquid hydrocarbon, wherein the second set of two or more microwave frequencies is greater than the first set of two or more microwave frequencies;

measuring the second set of two or more dielectric responses from the portion of the liquid hydrocarbon in response to the electromagnetic waves at the second set of two or more microwave frequencies; and determining a geochemical property of the liquid hydrocarbon in response to measurements of the first set of two or more dielectric responses and the second set of two or more dielectric responses, wherein each of the first plurality of predetermined temperatures and the second plurality of predetermined temperatures ranges between 20 deg. C. and 50 deg. C.

2. The method of claim 1, wherein the portion of the liquid hydrocarbon is maintained at the first plurality of predetermined temperatures during the step of measuring the first set of two or more dielectric responses and at the second plurality of predetermined temperatures during the step of measuring the second set of two or more dielectric responses.

3. The method of claim 1, wherein the liquid hydrocarbon is an oil separated from a production fluid containing brine and oil.

4. The method of claim 1, wherein the first microwave resonant cavity and the second microwave resonant cavity are of different sizes.

5. The method of claim 1, wherein each of the first microwave resonant cavity and the second microwave resonant cavity provides at least four microwave frequencies.

6. The method of claim 1, wherein each of the first set of two or more microwave frequencies and the second set of two or more microwave frequencies ranges from 100 MHz to 20 GHz.

7. The method of claim 1, wherein each of the first set of two or more microwave frequencies and the second set of two or more microwave frequencies ranges from 170 MHz to 8.6 GHz.

8. The method of claim 1, wherein the geochemical property is one or more of saturates content, aromatics content, resins content, or asphaltenes content of the liquid hydrocarbon.

9. The method of claim 1, wherein the geochemical property is heptane content, toluene content, or xylenes content, or toluene to heptane ratio, or xylenes to heptane ratio of the liquid hydrocarbon.

10. The method of claim 1, wherein the geochemical property is a ratio of metal content associated with porphyrins to sulfur content present in the liquid hydrocarbon.

11. A method for characterizing a geochemical property of a liquid hydrocarbon, the method comprising:

exposing a portion of a liquid hydrocarbon at a first predetermined temperature in a first microwave resonant cavity to electromagnetic waves at a first set of two or more microwave frequencies to elicit a first set of two or more dielectric responses from the portion of the liquid hydrocarbon;

measuring the first set of two or more dielectric responses from the portion of the liquid hydrocarbon in response to the electromagnetic waves at the first set of two or more microwave frequencies;

exposing the portion of the liquid hydrocarbon at the first predetermined temperature in a second microwave resonant cavity to electromagnetic waves at a second set of two or more microwave frequencies to elicit a second set of two or more dielectric responses from the portion of the liquid hydrocarbon, wherein the second set of two or more microwave frequencies is greater than the first set of two or more microwave frequencies;

measuring the second set of two or more dielectric responses from the portion of the liquid hydrocarbon in response to the electromagnetic waves at the second set of two or more microwave frequencies;

exposing the portion of the liquid hydrocarbon at a second predetermined temperature in the first microwave resonant cavity to electromagnetic waves at the first set of two or more microwave frequencies to elicit a third set of two or more dielectric responses from the portion of the liquid hydrocarbon;

measuring the third set of two or more dielectric responses from the portion of the liquid hydrocarbon in response to the electromagnetic waves at the first set of two or more microwave frequencies;

exposing the portion of the liquid hydrocarbon at a third predetermined temperature in the second microwave resonant cavity to electromagnetic waves at the second set of two or more microwave frequencies to elicit a fourth set of two or more dielectric responses from the portion of the liquid hydrocarbon;

measuring the fourth set of two or more dielectric responses from the portion of the liquid hydrocarbon in response to the electromagnetic waves at the second set of two or more microwave frequencies; and determining a geochemical property of the liquid hydrocarbon in response to measurements of the first set of two or more dielectric responses, the second set of two or more dielectric responses, the third set of two or more dielectric responses, and the fourth set of two or more dielectric responses, wherein each of the first predetermined temperature, the second predetermined temperature, and the third predetermined temperature ranges between 20 deg. C. and 50 deg. C., wherein the first predetermined temperature is less than the second predetermined temperature and the second predetermined temperature is less than the third predetermined temperature.

12. The method of claim 11, wherein the liquid hydrocarbon is an oil separated from a production fluid containing brine and oil.

13. The method of claim 11, wherein the first microwave resonant cavity provides five microwave frequencies.

14. The method of claim 11, wherein the second microwave resonant cavity provides four microwave frequencies.

15. The method of claim 11, wherein each of the first set of two or more microwave frequencies and the second set of two or more microwave frequencies ranges from 100 MHz to 20 GHz.

16. The method of claim 11, wherein the first set of two or more microwave frequencies ranges from 170 MHz to 2.3 GHz.

17. The method of claim 11, wherein the second set of two or more microwave frequencies ranges from from 1.3 GHz to 8.6 GHz.

18. The method of claim 11, wherein the geochemical property is one or more of saturates content, aromatics content, resins content, or asphaltenes content present in the liquid hydrocarbon.

19. The method of claim 11, wherein the geochemical property is one or more of toluene content, or xylenes content, heptane content, ratio of toluene to heptane, or ratio of xylenes to heptane present in the liquid hydrocarbon.

20. The method of claim 11, wherein the geochemical property is a ratio of metal content associated with porphyrins to sulfur content present in the liquid hydrocarbon.

* * * * *